United States Patent [19]

Burke

[11] Patent Number: 5,372,034
[45] Date of Patent: Dec. 13, 1994

[54] HIGH SOLIDS PAINT VISCOMETER

[75] Inventor: Thomas J. Burke, Los Gatos, Calif.

[73] Assignee: FMC Corporation, Chicago, Ill.

[21] Appl. No.: 77,261

[22] Filed: Jun. 17, 1993

[51] Int. Cl.$^5$ .............................................. G01N 11/04
[52] U.S. Cl. ................................. 73/54.11; 73/54.13
[58] Field of Search ................. 73/54.01, 54.04, 54.07, 73/54.11, 54.13

[56] References Cited

U.S. PATENT DOCUMENTS

| | | | |
|---|---|---|---|
| 1,502,118 | 7/1924 | Osborne | 73/54.13 |
| 2,141,329 | 12/1938 | Zahn | 73/54.11 |
| 2,564,892 | 8/1951 | Gerin | 73/54.11 |
| 2,836,975 | 6/1958 | Euverard | 73/54.11 |
| 4,065,959 | 1/1978 | Richardson | 73/54.13 |
| 4,400,973 | 8/1983 | Hegedus | 73/54.11 |
| 4,449,394 | 5/1984 | Hegedus | 73/54.04 |

OTHER PUBLICATIONS

Brochure from Paul N. Gardner Company, Inc. Entitled "Zahn Signature Series Viscosity Cups", dated Jun. 1987.

Primary Examiner—Thomas P. Noland
Assistant Examiner—Michael J. Brock
Attorney, Agent, or Firm—Michael Lee; R. C. Kamp; R. B. Megley

[57] ABSTRACT

The invention provides a viscosity cup with an upward extending tube or lip, which provides a cut off point for paint draining through an orifice, providing more consistent viscosity measurements.

4 Claims, 1 Drawing Sheet

U.S. Patent  Dec. 13, 1994  5,372,034
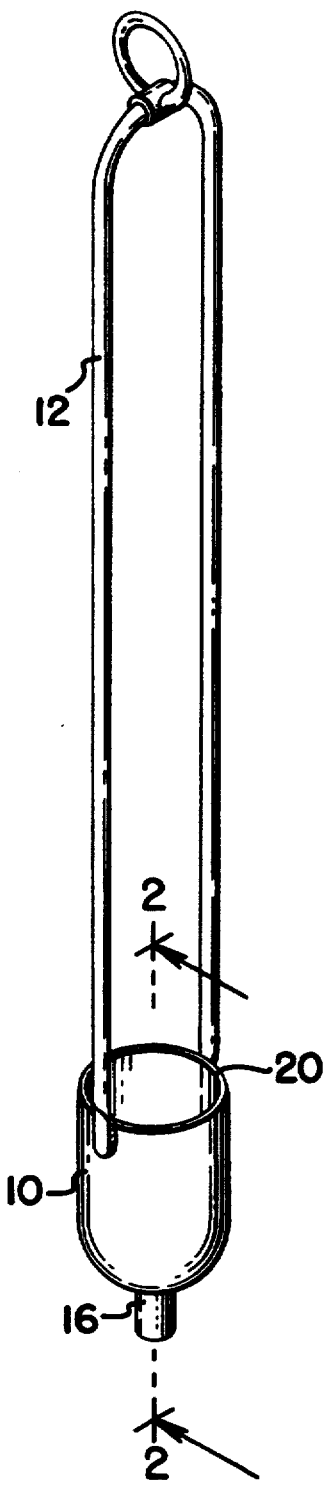
FIG_1
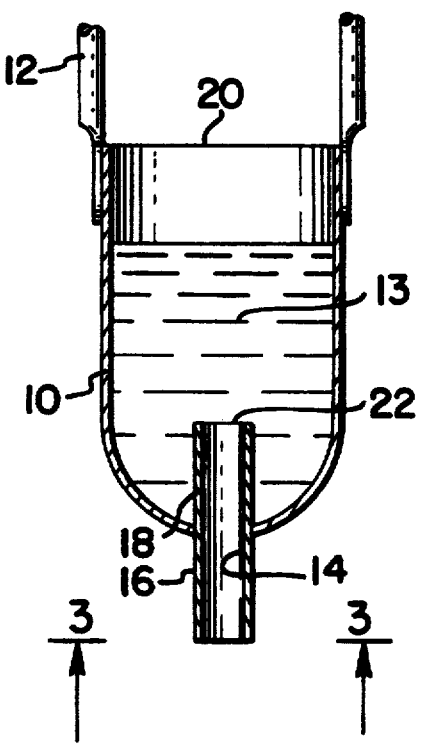
FIG_2
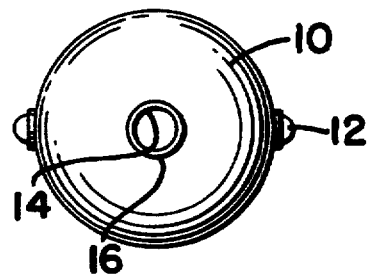
FIG_3

HIGH SOLIDS PAINT VISCOMETER

In the prior art a Zahn viscosity cup was used to measure the viscosity of paint. The viscosity cup was a cup with a hole on the bottom and a handle. The cup is filled with paint and the time it takes for the paint to pass through the hole and empty the cup was used to determine paint viscosity. Because of the shape of the cup and the hole, the paint which drains through the hole last, tends to cling to the inside of the cup, causing inconsistent measurements. In the prior are high viscosity paints would have an inconsistent first burble, causing the inconsistent measurements The invention provides a viscosity cup with an upward extending tube or lip, which provides a cut off point is for paint draining through an orifice, providing more consistent viscosity measurements.

FIG. 1 is a perspective view of a viscosity cup used in the preferred embodiment of the invention.

FIG. 2 is a cross-sectional view of the cup along lines 2—2 of FIG. 1.

FIG. 3 is an end view of the cup along lines 3—3 of FIG. 2.

FIG. 1 shows a cup 10 with a handle 12. FIG. 2 is a cross-sectional view of the cup 10 along lines 2—2 of FIG. 1 with the cup 10 containing paint 13. FIG. 3 is an end view of the cup 10 and the handle 12 long lines 3—3 of FIG. 2. The cup 10 has an orifice 14. The orifice 14 is adjacent to a first tube 18 extending into the cup 10. The orifice 14 is also adjacent to a second tube 16 extending to the outside of the cup 10. Both the first tube 18 and the second tube 16 surround the orifice 14. In the preferred embodiment, the first tube 16 and the second tube 18 are formed by a single tube.

in operation, the handle 12 is used to maneuver the cup 10 and lower the cup into a container of paint, allowing the cup 10 to be filled with paint 13. The time it takes for the top surface of the paint to go from the top 20 of the cup 10 to the top 22 of the second tube 18 is measured. The measured time indicates the viscosity of the paint 13.

The top 22 of the second tube 18 provides a cut off point for paint draining through the orifice 14. This cut off point provides more consistent measurements for the viscosity of paint, since the paint more consistently creates a first burble.

More consistent measurements for paint viscosity is important in the use of robotics for painting.

While a preferred embodiment of the present invention has been shown and described herein, it will be appreciated that various changes and modifications may be made therein without departing from the spirit of the invention as defined by the scope of the appended claims.

What is claimed is:

1. An apparatus for measuring the viscosity of a fluid, comprising:
   a cup with an inside and an outside, and with a bottom and top, with an orifice in the bottom of the cup;
   a handle mechanically connected to the cup; and
   a first tube extending to the inside of the cup wherein the tube surrounds the orifice.

2. An apparatus, as claimed in claim 1, further comprising, a second tube surrounding the orifice extending outside the cup.

3. An apparatus, as claimed in claim 2, wherein the first tube and the second tube form a single tube.

4. A method of measuring viscosity of a fluid, comprising:
   filling a cup with fluid;
   allowing the fluid to drain through an orifice in the cup;
   stopping the fluid from draining through the cup once a top surface of the fluid reaches a top lip of a tube surrounding the orifice, wherein the tube extends into the cup; and
   measuring the change in time from when the fluid begins draining through the orifice until the time that the fluid stops draining.

* * * * *